US008548560B2

(12) United States Patent
Saes et al.

(10) Patent No.: US 8,548,560 B2
(45) Date of Patent: Oct. 1, 2013

(54) ADAPTIVE DATA RATE CONTROL

(75) Inventors: Marc Paul Saes, Beek En Donk (NL);
Filips Van Liere, Eindhoven (NL);
Marinus Johannes Adrianus Maria Van Helvoort, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 125 days.

(21) Appl. No.: 12/994,172

(22) PCT Filed: May 28, 2009

(86) PCT No.: PCT/IB2009/052254
§ 371 (c)(1),
(2), (4) Date: Nov. 23, 2010

(87) PCT Pub. No.: WO2009/147596
PCT Pub. Date: Dec. 10, 2009

(65) Prior Publication Data
US 2011/0103491 A1 May 5, 2011

(30) Foreign Application Priority Data

Jun. 4, 2008 (EP) .................................. 08157556

(51) Int. Cl.
*A61B 5/05* (2006.01)
(52) U.S. Cl.
USPC .......................................... 600/407; 600/409
(58) Field of Classification Search
USPC ................... 600/407–429, 437–480
See application file for complete search history.

(56) References Cited

U.S. PATENT DOCUMENTS

| 4,991,587 | A * | 2/1991 | Blakeley et al. ............... 600/483 |
| 5,384,536 | A * | 1/1995 | Murakami et al. ............ 324/309 |
| 6,339,717 | B1 * | 1/2002 | Baumgartl et al. ........... 600/407 |
| 6,356,780 | B1 * | 3/2002 | Licato et al. ................... 600/407 |
| 7,123,009 | B1 * | 10/2006 | Scott .............................. 324/311 |
| 7,457,804 | B2 * | 11/2008 | Uber et al. ............................ 1/1 |
| 7,996,381 | B2 * | 8/2011 | Uber et al. .................... 707/708 |
| 8,093,900 | B2 * | 1/2012 | Bennett ......................... 324/322 |
| 8,155,101 | B2 * | 4/2012 | Van Helvoort et al. ........ 370/345 |
| 2003/0212707 | A1 * | 11/2003 | Uber et al. ................. 707/104.1 |
| 2005/0008074 | A1 | 1/2005 | Van Beek et al. |
| 2005/0107681 | A1 * | 5/2005 | Griffiths ........................ 600/410 |
| 2006/0100860 | A1 * | 5/2006 | Oppelt ........................... 704/201 |
| 2006/0198392 | A1 | 9/2006 | Park et al. |

(Continued)

FOREIGN PATENT DOCUMENTS

| WO | 2004102949 A1 | 11/2004 |
| WO | 2006030331 A2 | 3/2006 |
| WO | 2006048816 A1 | 5/2006 |

OTHER PUBLICATIONS

Putra et al: "Cross Layer Design of Wireless LAN for Telemedicine Application"; 2009 Third Asia International Conference on Modelling & Simulation, May 2009, pp. 264-269.

*Primary Examiner* — Sanjay Cattungal

(57) ABSTRACT

A data rate controlling feedback loop evaluates an actual instantaneous available quality of service of a communication link for transmitting data and controls the data rate based on an evaluation result, Feedback control may both be local to a device for acquiring examination data, such as a magnetic resonance imaging coil, or over the communication link by reducing the data rate at least momentarily to fit the communication link's performance over time, enabling a graceful degradation of an image quality at lower data rates.

14 Claims, 3 Drawing Sheets

(56) References Cited

U.S. PATENT DOCUMENTS

| | | |
|---|---|---|
| 2006/0270433 A1* | 11/2006 | Kelton et al. ............... 455/522 |
| 2006/0279284 A1* | 12/2006 | Vaughan ..................... 324/318 |
| 2008/0028083 A1* | 1/2008 | Rezvani et al. ............... 709/229 |
| 2009/0005669 A1* | 1/2009 | Schmidt et al. ............... 600/407 |
| 2009/0070342 A1* | 3/2009 | Uber et al. ..................... 707/10 |
| 2011/0270633 A1* | 11/2011 | Uber, III et al. ................. 705/3 |

* cited by examiner

ADAPTIVE DATA RATE CONTROL

FIELD OF THE INVENTION

The present invention generally relates to a device, system, method and computer program for adaptively controlling a data rate based on an available quality of service of a communication link, in particular for use with wireless magnetic resonance imaging (MRI) coils.

BACKGROUND OF THE INVENTION

Several manufacturers of MRI systems currently try to develop pure cordless/wireless MRI coils. A prerequisite for such wireless MRI coils is that an analog magnetic resonance (MR) signal (in the case of an analog coil) or acquired MR data (in the case of a digital coil) can be transported to a MR examination system via a high-speed wireless communication link.

A wireless communication link has a certain quality of service (QoS) with respect to latency and bandwidth properties of such a link. In real life, a performance of a wireless data transport depends to a large extent on an actual transfer response of a wireless channel used to perform the data transport. The actual transfer response can vary largely in a relatively small time due to e.g. movements of antennas caused for instance by a patient movement. An antenna movement can lead to reflections or absorptions in the radio frequency (RF) domain that may impact a momentary signal-to-noise ratio (SNR) of the wireless channel. This can degrade the communication link at least temporary. In addition, noise from other (or own) equipment may temporarily degrade the communication link as well.

If a number of MRI coil elements/channels increases, a required MR data rate also increases. It is a precondition for an effective usage of wireless MRI systems that the required MR data rate and also a required wireless transport power dissipation can be achieved. In view of the currently available wireless technologies, it may be expected that at least during the next 5 to 10 years these technologies will be a blocking factor for the number of channels that can be sensibly placed in or associated with a MRI coil.

When the actual transport technology is the blocking factor, it would be advantageous to at least get the most out of an available (varying) bandwidth and latency. This can be achieved by a MR-signal-aware lossless compression, but also by compressions with limited loss. However, this may still not suffice to achieve a smooth operation of a wireless MRI system. Acquired MR data should leave the MRI coil as soon as possible after acquiring it, since storing the MR data would require huge amounts of power-dissipating and volume-consuming memory at the MRI coil. Further, with the currently available wireless technologies a performance of the communication link can drop below a certain minimum threshold at some points in time, after which the acquired MR data are simply lost. This is not acceptable from a MRI perspective. It may even be necessary to abort a MRI scan.

When using a wireless MRI coil, another issue to be resolved is to enable a robust wireless control of a MR receiver at the MRI coil with respect to its settings over time. That is, to ensure that control information can be reliably transmitted to the MR receiver is an issue to be resolved.

SUMMARY OF THE INVENTION

It is an object of the present invention to provide an adaptive data rate control yielding an improved performance with an available communication link.

Accordingly, in a first aspect of the present invention a device is presented. The device comprises an acquisition unit configured to acquire examination data, a communication unit configured to transmit the examination data via a communication link and receive control information via the communication link, and an adaptation unit configured to adapt a data rate of the examination data, based on an available quality of service of the communication link, wherein the acquisition unit and/or the adaptation unit is configured to be controlled based on the control information. Thus, a data rate as high as possible for given communication conditions can be achieved. Hence, an improved performance may be attained with an available communication link. That is, the data transmission for an actual available quality of service can be optimized. Further, there is no need to abort an acquisition procedure under bad communication conditions. In addition, a remote control of the device and its acquisition unit and/or adaptation unit over some kind of network is enabled, for example by means of a central control unit transmitting control information via a wireless transport medium.

In a second aspect of the present invention the acquisition unit is configured to perform a compression of the examination data, and the adaptation unit is configured to adapt a degree of the compression. Thus, a higher degree of the compression can be chosen for a lower quality of service and vice versa. In this way, as many information as possible for a certain quality of service may be transmitted. The second aspect can be combined with the first aspect.

In a third aspect of the present invention the adaptation unit is configured to instruct the acquisition unit to perform no compression or a lossless compression of the examination data if the available quality of service is above a certain limit and instruct the acquisition unit to perform a lossless compression with a higher compression ratio than in case of the available quality of service being above the certain limit or a lossy compression of the examination data if the available quality of service is equal to or below the certain limit. Thus, a lossy compression can be avoided when a sufficient transmission bandwidth is available. On the other hand, the transmission may not be affected when less transmission bandwidth is available. The third aspect can be combined with the first or second aspect.

In a fourth aspect of the present invention the adaptation unit is configured to adapt an acquisition rate of the acquisition unit. In case that less transmission bandwidth is available, a data throughput may be decreased by reducing the acquisition rate. Thus, a continuous data transmission can be ensured. The fourth aspect may be combined with any one of the preceding aspects.

In a fifth aspect of the present invention the adaptation unit is configured to instruct the acquisition unit to drop at least one examination data acquisition window. By dropping an examination data acquisition window, less examination data are acquired in a certain time interval. Therefore, a data throughput can be reduced, enabling a continuous data transmission despite of a lower transmission bandwidth. The fifth aspect may be combined with any one of the preceding aspects.

In a sixth aspect of the present invention the adaptation unit is configured to adapt a compression ratio of the examination data if the available quality of service is equal to or below a first limit and adapt an acquisition rate of the acquisition unit if the available quality of service is equal to or below a second limit. Thus, it is possible to use a local feedback to reduce a data rate of the examination data by increasing the compression ratio as long as a sufficient available quality of service can be achieved by such measure. In case that the available quality of service is insufficient even with a maximum compression ratio, a global feedback can be used to slow down an acquisition of the examination data and/or retry acquisition windows in order to reduce the data rate. The sixth aspect may be combined with any one of the preceding aspects.

In a seventh aspect of the present invention the device further comprises a data buffer unit configured to buffer the examination data and supply a fill rate and level, wherein the communication unit is configured to transmit the buffered examination data, and wherein the adaptation unit is configured to determine the available quality of service based on the fill rate and level supplied by the data buffer unit. Buffering the examination data enables some flexibility in transmitting the data. That is, data may be transmitted at a higher transmission rate if an instantaneous available bandwidth is higher and at a lower transmission rate if the instantaneous available bandwidth is lower, irrespective of a data acquisition rate data at a respective time. The seventh aspect may be combined with any one of the preceding aspects.

In an eighth aspect of the present invention the device further comprises a control buffer unit configured to buffer the received control information and supply a fill rate and level, and a backup control unit configured to determine the available quality of service based on the fill rate and level supplied by the control buffer unit, ascertain whether the available quality of service is below a backup limit and control the acquisition unit if the ascertainment is affirmative, wherein the acquisition unit is configured to be controlled based on the buffered control information. This enables to control one or more acquisition units or receivers when the quality of service becomes so low that the control information from a remote control unit is missing at some point. The eighth aspect may be combined with any one of the preceding aspects.

In a ninth aspect of the present invention the device is a wireless magnetic resonance imaging coil. Thus, the device can be easily integrated into an existing wireless magnetic resonance imaging system. The ninth aspect may be combined with any one of the preceding aspects.

In a tenth aspect of the present invention a system is presented. The system comprises at least one device according to any one of the preceding aspects, and a control device configured to transmit control information to the at least one device and receive the examination data from the at least one device. The system enables improved communications of examination data and control information between the at least one device and the control device. On the one hand, a continuous transmission of the examination data to the control device under difficult communication conditions can be ensured. On the other hand, a robust (wireless) remote control of the at least one device is possible.

In an eleventh aspect of the present invention the control device is configured to throttle the communication link if the available quality of service is equal to or below a first threshold, and the adaptation unit is configured to perform a local reduction of the data rate if the available quality of service is equal to or below a second threshold. Thus, in case the quality of service meets some minimum conditions, an image quality can be maintained albeit at a lower image throughput, and in case of an extreme communication link deterioration still a local or autonomous reduction of the data rate with a reduced image quality may be performed. Thus, there is no need to abort a data acquisition procedure. The eleventh aspect may be combined with the tenth aspect.

In a twelfth aspect of the present invention the system is a magnetic resonance imaging system, and the control device is configured to control an acquisition rate of the at least one device by at least one of changing future acquisition transmission cycles of the examination data and changing a current supplied to magnetic field gradient coils of the magnetic resonance imaging system. This offers different possibilities to reduce the future bandwidth demand by reducing the acquisition rate, enabling a continuous data transmission despite of a degraded quality of service. The twelfth aspect may be combined with the tenth or eleventh aspect.

In a thirteenth aspect of the present invention a method is presented. The method comprises acquiring examination data, transmitting the examination data via a communication link, and adapting a data rate of the examination data, based on an available quality of service of the communication link. Thus, a data rate as high as possible for given communication conditions can be achieved. Hence, an improved performance may be attained with an available communication link. That is, the data transmission for an actual available quality of service can be optimized. Further, there is no need to abort an acquisition procedure under bad communication conditions.

In a fourteenth aspect of the present invention a computer program is presented. The computer program comprises program code means for causing a computer to carry out the steps of a method according to the thirteenth aspect when the computer program is carried out on a computer. Thus, the same advantages as with the method according to the thirteenth aspect can be achieved.

Further advantageous modifications are defined in the dependent claims.

BRIEF DESCRIPTION OF THE DRAWINGS

These and other aspects of the present invention will be apparent from and elucidated by an embodiment described hereinafter, by way of example, with reference to the accompanying drawings, in which.

DETAILED DESCRIPTION OF AN EMBODIMENT

Figure 1:
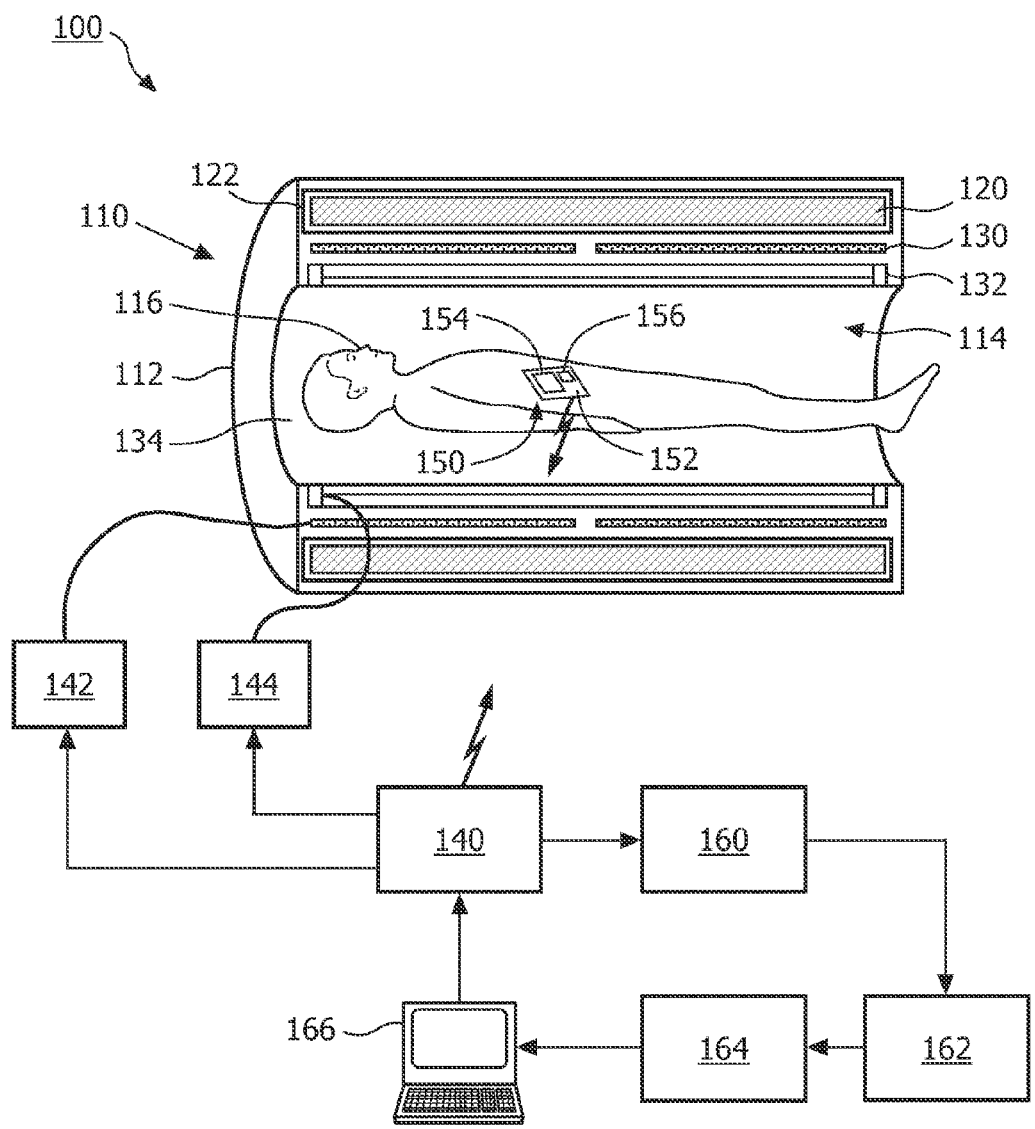
FIG. 1 shows a schematic diagram illustrating a basic arrangement of an exemplary system according to the embodiment.

FIG. 1 shows a schematic diagram illustrating a basic arrangement of an exemplary system 100 according to the embodiment. A magnetic resonance imaging (MRI) system is depicted in FIG. 1. However, the following description is to be considered illustrative or exemplary and not restrictive. Other application areas such as alternative kinds of examination or imaging systems like e.g. x-ray systems are possible.

A MRI scanner 110 can include a housing 112 defining a generally cylindrical scanner bore 114 inside of which an imaging subject 116 like a human or animal body may be disposed. Main magnetic field coils 120 can be disposed inside the housing 112. The main magnetic field coils 120 may be superconducting coils disposed inside a cryoshrouding 122. Resistive main magnets can also be used. The housing 112 may also house or support magnetic field gradient coils 130 for selectively producing magnetic field gradients in the scanner bore 114. The housing 112 can further house or support a radio frequency (RF) coil 132 such as e.g. a body coil, a head coil, a surface coil or another local coil for selectively exciting magnetic resonances. The housing 112 can include a cosmetic inner liner 134 defining the scanner bore 114.

The main magnetic field coils 120 may produce a main magnetic field $B_0$ directed generally parallel to a cylinder axis of the scanner bore 114. A control device 140 such as e.g. a central control device, a MR experiment control device or a MRI controller can operate magnetic field gradient controllers 142 to selectively energize the magnetic field gradient coils 130, and operate a RF transmitter 144 coupled to the RF coil 132 to selectively inject RF excitation pulses into the imaging subject 116. By selectively operating the magnetic field gradient coils 130 and the RF coil 132, a magnetic resonance may be generated and spatially encoded in at least a portion of a region of interest of the imaging subject 116. By applying selected magnetic field gradients via the gradient coils 130, a selected k-space trajectory can be traversed, such as a Cartesian trajectory, a plurality of radial trajectories, a spiral trajectory and so forth.

During an imaging data acquisition, the control device 140 may operate a device 150. The device 150 can be a RF reception coil such as e.g. a wireless MRI coil or an array of similar local coils. The device 150 may be disposed inside the scanner bore 114 and close to or in contact with the imaging subject 116. It can be battery-powered or comprise a rechargeable accumulator. While a single surface coil is shown in FIG. 1, in some applications a plurality of surface coils may be employed in a phased array or other configuration. Moreover, the device 150 can be embodied by other local coils besides a surface coil. For example, the device 150 can be a head coil that surrounds the head, a knee coil and so forth.

The device 150 may comprise a common substrate or support 152 on or in which a RF reception antenna 154 is disposed. Also it is not shown in FIG. 1, the device 150 can also include an antenna for wireless communications with the control device 140. Alternatively, the antenna 154 may be used for such communications. The antenna 154 can be tuned to a frequency of the magnetic resonance generated by the combination of RF excitation and applied magnetic field $B_o$ and have a bandwidth spanning at least a magnetic resonance (MR) frequency encoding bandwidth. Thus, the antenna 154 may detect generated MR signals. Electronics 156 can be disposed on or in the common substrate or support 152. The electronics 156 may be capable of a dynamic compression of the detected MR signals and other signal processing such as e.g. an analog-to-digital conversion, a conversion to a wireless or wired transmission medium like a RF transmission medium or an infrared transmission medium, and so forth. In real life at least a wireless transport medium is a lossy one. Further, the electronics 156 can generate MR data and have other functionality described in more detail below. For example, a compressed signal may be digitized at the device 150 and transmitted to the control device 140 in a floating point or other digital format that intrinsically incorporates the compression. The compressed signal can also be transmitted to the control device 140 along with information about the compression, and the compressed signal may be decompressed at the control device 140 using the transmitted compression information.

The electronics 156 may be disposed in an electronics module. Although it is not shown in FIG. 1, the device 150 can be disposed in a protective housing or cover, encased in a waterproof layer, can include a soft padding, securing straps and so forth, or may be otherwise configured for cosmetic, safety, patient comfort or other considerations.

In the surface coil illustrated as an example of the device 150 in FIG. 1, the common support 152 is a generally planar substrate, and the antenna 154 can be, for example, copper or other electrically conductive traces formed on the substrate 152. The electronics 156 may be disposed on or in one of the conductors of the antenna 154. In arrangements where the antenna 154 is defined by rings, rungs or other non-planar components such as with e.g. a head coil, a knee coil or the like, the electronics 156 can be suitably disposed directly on one or more of antenna components, or may be attached therewith as a unitary structure via a suitable additional support structure.

The device 150 can output an analog or digital electrical or optical signal. This signal can be transmitted to the control device 140 by means of a wireless or wired communication link. For example, RF or infrared communications may be utilized. In FIG. 1 a wireless communication link is depicted as one example. The signal transmitted by the device 150 can be received by an antenna, an infrared detector or another reception element (not shown in FIG. 1) of the control device 140.

The transmitted signal may be received at the control device 140 and dynamically decompressed (if it was transmitted in a compressed format) to recover the MR signal, MR samples or MR data. The control device 140 can demodulate the signal and optionally perform further processing to produce MR data. The MR data may be stored in a MR data memory 160. The MR data can be reconstructed by a reconstruction processor 162 into an image representation using a Fourier transform-based reconstruction algorithm, a filtered backprojection-based reconstruction algorithm or another suitable image reconstruction algorithm. The reconstructed image or images generated by the reconstruction processor 162 may be stored in an image memory 164 and can be displayed on a user interface 166, stored in non-volatile memory, transmitted over a local intranet or the Internet, viewed, stored, manipulated and so forth. The user interface 166 may enable a radiologist, technician or other operator of the MRI scanner 110 to communicate with the control device 140 to select, modify and execute MRI sequences.

Figure 2:
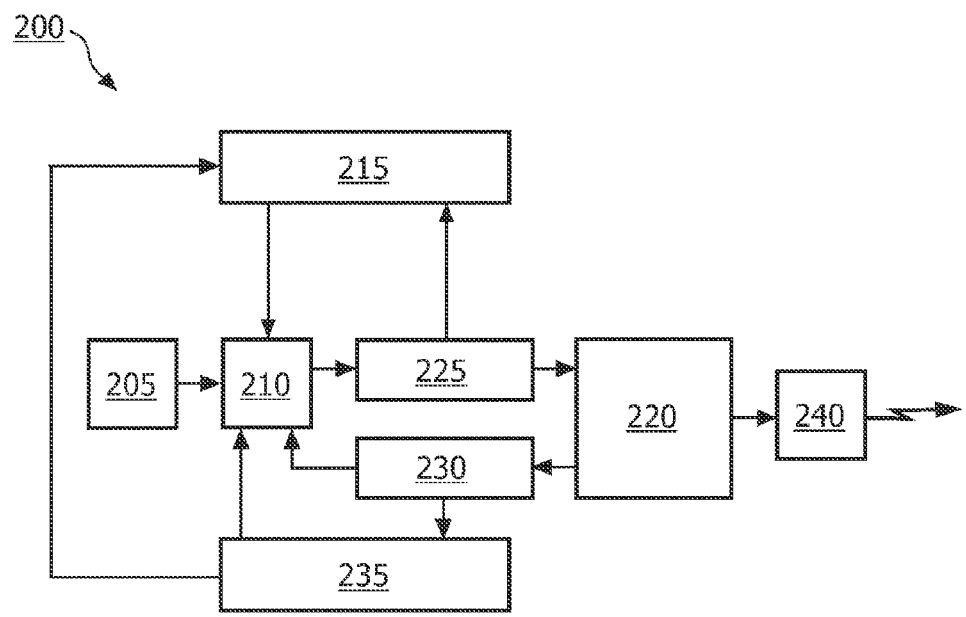
FIG. 2 shows a schematic block diagram illustrating an exemplary device according to the embodiment.

The described MRI system 100 is an illustrative example only. Various modifications are possible. For example, the MRI scanner 110 as shown in FIG. 1 is a horizontal bore scanner. However, substantially any type of MRI scanner can be used, including but not limited to vertical bore scanners, open magnet scanners and so forth. FIG. 2 shows a schematic block diagram illustrating an exemplary device 200 according to the embodiment. The device 200 corresponds to the device 150 shown in FIG. 1. It can comprise a first antenna 205 corresponding to the antenna 154 in FIG. 1, an acquisition unit 210 such as e.g. a MR receiver, an adaptation unit 215 and a communication unit 220. Further, the device 200 may include a data buffer unit 225 such as e.g. a first-in-first-out (FIFO) memory, a control buffer unit 230 such as e.g. a FIFO memory, and a backup control unit 235. In addition, a second antenna 240 can be provided. The components 210 to 235 correspond to the electronics 156 shown in FIG. 1.

The first antenna 205 can detect MR signals. The acquisition unit 210 may process the MR signals and acquire examination data such as MR data, based on the detected MR signals. That is, it can be a source of acquired MR data. The processing performed by the acquisition unit 210 can include a digitization or sampling of the MR signals, a compression of obtained MR samples and so forth. Acquired examination data can be transmitted by the communication unit 220 via a communication link and received by a control device not shown in FIG. 2 and corresponding to the control device 140 depicted in FIG. 1. The second antenna 240 may be used to transmit the examination data. Alternatively, the examination data can be transmitted via the first antenna 205, for example by using some kind of multiplexing such as e.g. a frequency-division multiple access (FDMA) or time-division multiple access (TDMA) procedure.

The acquired data may be buffered in the data buffer unit 225 prior to transmitting them by means of the communication unit 220. The data buffer unit 225 can have a fill rate and level output. That is, it may supply a fill rate and a fill level indicating how fast the data buffer unit 225 is filled with examination data and which percentage thereof has already been filled.

The processing and data acquisition performed by the acquisition unit 210 can be adjusted or adapted by the adaptation unit 215. In particular, a data rate of the examination data may be adapted based on an available quality of service (QoS) of the communication link used to transmit the examination data. For example, the data rate can be adapted in dependence on an instantaneous available bandwidth and/or latency of the communication link. The adaptation unit 215 may determine the available quality of service on the basis of the fill rate and level supplied by the data buffer unit 225. For example, a high fill level can be indicative of a low available quality of service since the data buffer unit 225 may be fuller than usual if the bandwidth of the communication link is not sufficient or a latency thereof has increased and, therefore, data are retained in the data buffer unit 225 longer than usual. Also, a high fill rate can be indicative of a low available quality of service since the data buffer unit 225 may fill faster if the data cannot be transmitted by the communication unit 220 as quick as usual due to a lack of bandwidth or a high latency of the communication link. Even if it is not illustrated in FIG. 2, the adaptation unit 215 may also determine the available quality of service based on a fill rate and level supplied by the control buffer unit 230 as described below.

If the available quality of service of the communication link is sufficient, there may be no need for special measures. In this case, no compression at all or a lossless compression can be applied to the examination data, i.e. a normal operation may be performed. Different approaches for reducing the data rate of the examination data can be applied if the available quality of service of the communication link is too low, i.e. insufficient. These approaches may be used simultaneously and can also be applied separately.

A first approach may be to adapt a compression ratio or degree of compression by using a local feedback loop. For example, the compression ratio can be increased when the available quality of service decreases. If the available quality of service is above a certain threshold or limit, the adaptation unit 215 may instruct the acquisition unit 210 to perform no compression or a lossless compression. If the available quality of service is equal to or below the certain limit, the adaptation unit 215 can instruct the acquisition unit 210 to perform a compression suitable to reduce the data rata of the examination data, i.e. a lossless compression with a higher degree of compression or even a lossy compression, which may reduce the data rate.

For example, the acquisition unit 210 can perform no compression at all if the available quality of service is above a first limit and perform a lossless or lossy compression if the available quality of service is equal to or below the first limit. Alternatively, the acquisition unit 210 can perform a lossless compression with a certain compression ratio if the available quality of service is above the first limit and perform a lossy compression or a lossless compression with a compression ratio higher than the certain compression ratio if the available quality of service is equal to or below the first limit. Further, the acquisition unit 210 can perform no compression if the available quality of service is above a first limit, execute a lossless compression with a certain compression ratio if the available quality of service is equal to or below the first limit but above a second limit, and perform a lossless compression with a compression ratio higher than the certain compression ratio or a lossy compression if the available quality of service is equal to or below the second limit. Alternatively, the acquisition unit 210 may execute a lossless compression with a certain compression ratio if the available quality of service is above the first limit, perform a lossless compression with a compression ratio higher than the certain compression ratio if the available quality of service is equal to or below the first limit but above the second limit, and perform a lossy compression if the available quality of service is equal to or below the second limit. Moreover, the acquisition unit 210 can perform no compression if the available quality of service is above a first limit, execute a lossless compression with a certain compression ratio if the available quality of service is equal to or below the first limit but above a second limit, perform a lossless compression with a compression ratio higher than the certain compression ratio if the available quality of service is equal to or below the second limit but above a third limit, and execute a lossy compression if the available quality of service is equal to or below the third limit.

As discussed above, there can be a plurality of operating regimes depending on the available quality of service, with respective limits between adjacent operating regimes. Up to four operating regimes and up to three limits are described above. However, this description is merely exemplary. More advanced techniques may define more operating regimes and corresponding quality of service limits. For example, there can be a plurality of operating regimes in which lossless compressions with different compression ratios are performed, and/or a plurality of operating regimes in which lossy compressions with different compression ratios are executed, with respective limits between adjacent operating regimes. By defining such additional operating regimes and limits, an operating regime of a lossless compression and/or an operating regime of a lossy compression as described above may be subdivided.

The first approach can potentially be autonomous, i.e. locally applied at the device 200 without the need for any instructions from a remote device such as the control device 140. It can yield a substantially immediate reduction of the data rate. The compression may be applied to the examination data before supplying them from the acquisition unit 210 to the data buffer unit 225. A lossy compression can be performed by e.g. removing lowest bits from the examination data, reducing a sampling rate with averaging and so forth. The control device 140 may be informed on an actual compression ratio, which can be effected later and may be achieved e.g. by transmitting information about the compression together with compressed examination data. Thus, a corrective reacquisition of examination data can take place. Such reacquisition may be instructed by the control device 140 and performed by the acquisition unit 210. Further, a user can be informed or notified when an image quality threshold is not met. For example, some warning message or sound may be output by means of the user interface 166.

A second approach for reducing the data rate of the examination data may be to change future acquisition transmission cycles of examination data if the available quality of service of the communication link is too low, i.e. the communication link is not capable of transferring acquired examination data in a timely manner. In this case, an amount of examination data acquired in a certain period of time, i.e. an acquisition rate, can be reduced in order to enable a transmission of the acquired examination data with the available quality of service. The second approach may be used e.g. if the available quality of service is insufficient even with a maximum compression ratio. For example, each of the above-discussed arrangements having a plurality of operating regimes and quality of service limits can be provided with an additional limit at a lower end of a lowest operating regime, and the second approach may be applied if the available quality of service is equal to or below this additional limit. If only a first limit is present, an additional second limit at a lower end of an operating regime below the first limit can be defined. If first and second limits exist, an additional third limit at a lower end of an operating regime below the second limit may be specified. If first to third limits are present, an additional fourth limit at a lower end of an operating regime below the third limit can be defined. If more than three operating limits exist, an additional limit at a lower end of an operating regime below the respective last limit may be specified.

According to a first option, the acquisition rate of examination data can be reduced e.g. by dropping an examination data acquisition window and optionally reacquiring missed examination data later. That is, the adaptation unit 215 may instruct the acquisition unit 210 to drop an examination data acquisition window. This can be done in response to a decision taken locally (e.g. by the adaptation unit 215) or a corresponding instruction from the control device 140. Thus, a future data transmission rate may be reduced by acquiring less examination data. In this connection, it should be cared for maintaining a spin state control as required for MR imaging. That is, it should be ensured that a MR pulse sequence is continued. If an examination data acquisition window has been dropped, it does not necessarily have to be retried or repeated. An obligation to retry a dropped examination data acquisition window can depend on a current situation. For example, if a detailed examination of a human organ such as e.g. a liver or a kidney is performed, there may be an obligation to retry a dropped examination data acquisition window. In other cases, no such obligation can exist. Whether or not a dropped examination data acquisition window is to be retried may be decided by the control device 140, i.e. by using a global feedback loop.

A second option for reducing the acquisition rate can be to adjust magnetic field gradients and/or an acquisition timing. One possibility may be to dim or reduce a current supplied to the magnetic field gradient coils 130 while maintaining the spin state control. This can be achieved by operating the magnetic field gradient controllers 142 accordingly. That is, the control device 140 can instruct the magnetic field gradient controllers 142 to supply less current to the magnetic field gradient coils 130. This can result in a slower excitation of nuclei in the imaging subject 116 and, therefore, a longer acquisition cycle. Thus, it may take more time to acquire a set of examination data. Hence, the acquisition may be slowed down and the acquisition rate or data rate can be reduced.

By using one or both of the above two options, i.e. dimming or reducing the current and/or future data streams, the required bandwidth for the communication link may be reduced by taking more time for the scan, without any other side-effects. In a more severe situation the second approach can enable a continuous scanning with a graceful degradation of the image quality. Thus, a continuing workflow may be achieved and there is no need to stop the system 100 or MRI scanner 110. The user can be informed about the degraded image quality, for example by also transferring an actual compression ratio to a user level and indicating the same e.g. at the user interface 166. The image quality may rise again when allowed for by the available quality of service of the communication link.

The global feedback loop can be used to throttle the communication link such that the image quality can be maintained albeit at a lower image throughput. The local feedback loop may then only be used in case of an extreme communication link deterioration. In other words, the control device 140 can throttle the communication link if the available quality of service is equal to or below a first limit or threshold but above a second limit or threshold. This may be achieved by reducing the data rate e.g. according to the above-described second option, i.e. by adjusting the magnetic field gradients and/or the acquisition timing. On the other hand, the adaptation unit 215 can perform a local or autonomous reduction of the data rate if the available quality of service is equal to or below the second threshold. This may be achieved by reducing the data rate e.g. according to the above-described first option, i.e. by dropping examination data acquisition windows.

When both of the first and second approaches are employed, the first approach may be used if the available quality of service is equal to or below a certain threshold or limit, and the second approach can be used if the available quality of service is equal to or below a further threshold or limit. The certain limit can be e.g. a first limit above which a normal operation is performed. The further limit may be lower than the certain one and correspond to e.g. the above-described additional limit used to trigger an application of the second approach. That is, the adaptation unit 215 can adapt a compression ratio or degree of compression of examination data if the available quality of service is equal to or below the certain limit and adapt an acquisition rate of the acquisition unit 210 if the available quality of service is equal to or below the further limit.

For example, the further limit may be lower than the certain limit. If the available quality of service is above the certain limit, it can be sufficient. In this case, there may be no need for special measures. Thus, no compression at all or a lossless compression of examination data can be performed. If the available quality of service is equal to or below the certain limit but above the further limit, it may be insufficient. However, a lossless compression with a higher compression ratio or even a lossy compression of examination data can be acceptable. Hence, a lossy compression or a lossless compression with a higher compression ratio than in case of a sufficient available quality of service may be performed. That is, the first approach can be applied. If the available quality of service is equal to or below the further limit, it may be insufficient even with a maximum compression ratio. Thus, the second approach can be used to slow down the acquisition and/or retry acquisition windows. For example, the acquisition unit 210 may perform no compression if the available quality of service is above a first limit, execute a lossless compression if the available quality of service is equal to or below the first limit but above a second limit, perform a lossy compression if the available quality of service is equal to or below the second limit but above a third limit, and drop examination data acquisition windows if the available quality of service is equal to or below the third limit. Alternatively, the acquisition rate can be reduced by adjusting the magnetic field gradients and/or the acquisition timing if the available quality of service is equal to or below the third limit. Moreover, other arrangements are conceivable. For example, the further limit may be higher than the certain limit.

Hence, it is possible to use a local feedback in accordance with the first approach to reduce a data rate of the examination data by increasing the compression ratio as long as a sufficient available quality of service can be achieved by such measure. In case that the available quality of service is insufficient even with a maximum compression ratio, a global feedback in accordance with the second approach may be used to slow down an acquisition of the examination data and/or retry acquisition windows in order to reduce the data rate.

The communication unit 220 can not only transmit examination data but also receive control information by means of the second antenna 240 or the first antenna 205. The control information may be applied to control e.g. the acquisition unit 210 or the adaptation unit 215. It can be transmitted by a control device such as the control device 140 and may be buffered in the control buffer unit 230 prior to applying it for control purposes. The control buffer unit 230 can have a fill rate and level output. That is, it may supply a fill rate and a fill level indicating how fast the control buffer unit 230 is filled with control information and which percentage thereof has already been filled.

The backup control unit 235 can have the acquisition unit 210 or multiple acquisition units continue in an acquisition cycle that they were in before a communication loss. That is, the backup control unit 235 may take over the control if the quality of service of the communication link becomes so low that no control information can be received over the communication link. Thus, a continuous scanning can be ensured in this case. A control performed by the backup control unit 235 may be defined by the control information in the control buffer unit 230 that have been received before the communication loss, in a kind of repetitive scripting method. For example, a previous MR pulse sequence can be repeated. In this way, a continuous scanning may be achieved. By already filling the control buffer unit 230 with future control information, at least short interruptions in communication can be handled. To inform a MR examination system about a potential autonomous control by means of the backup control unit 235, this control information can be fed back to the MR examination system, e.g. the control device 140, via the same path as used for the examination data.

The backup control unit 235 may determine the available quality of service or bandwidth of the communication link on the basis of the fill rate and level supplied by the control buffer unit 230. Even if it is not illustrated in FIG. 2, this can also be done based on the fill rate and level supplied by the data buffer unit 225. Further, the backup control unit 235 can determine or ascertain based on the fill rate and level whether the available quality of service of the communication link is below a backup threshold or limit and control the acquisition unit 210 and/or the adaptation unit 215 if the ascertainment is affirmative or positive. That is, in case of a sufficient quality of service the control information from a central control unit such as the control unit 140 may be used to determine settings of the acquisition unit 210 and/or the adaptation unit 215, and in case of an insufficient quality of service control information provided by the backup control unit 235 can be used to determine these settings. The backup limit may correspond to the above-described additional limit used to trigger an application of the second approach or can differ from the same.

The backup control unit 235 may communicate with the adaptation unit 215 in order to choose between 1) dropping examination data acquisition windows completely (in case of an extreme communication link deterioration), 2) performing a lossless/lossy compression (in case of a moderate communication link deterioration), and 3) normal operation (in case of no communication link deterioration). If the backup control unit 235 is used, it can repeat a (previous) examination data acquisition window if the communication link is not capable of a timely transfer of acquired examination data and/or of control data for the next examination data acquisition window. This may allow to reduce the data rate without adjusting the magnetic field gradients and/or the acquisition timing, both of which could alter image content, in particular image contrast, and affect diagnostic value other than image quality (SNR and resolution).

Figure 3:
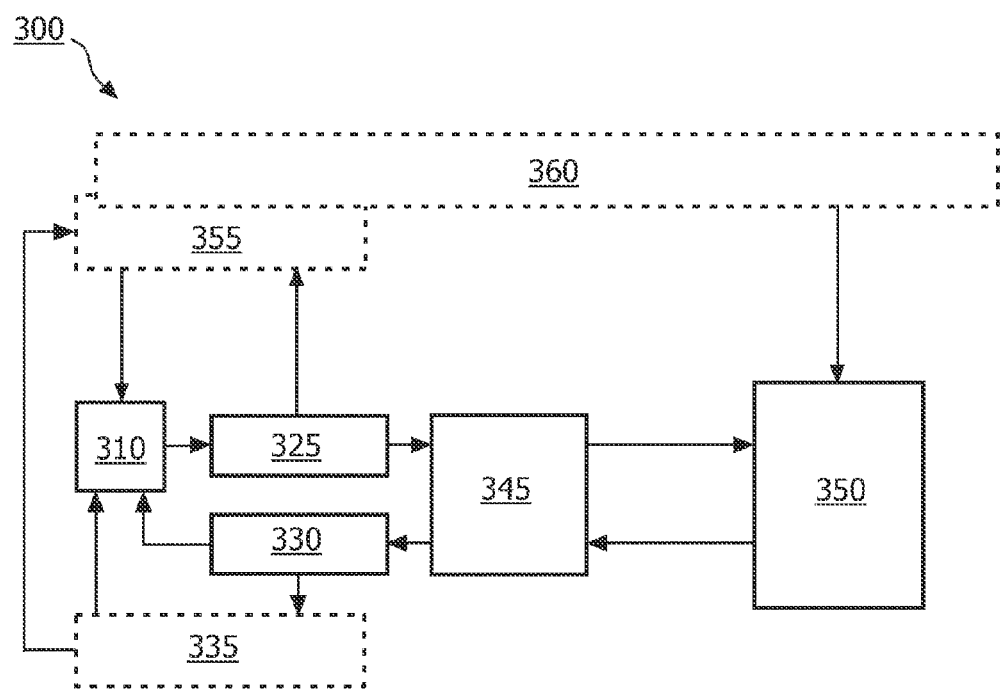
FIG. 3 shows a schematic block diagram illustrating a basic arrangement of exemplary feedback paths according to the embodiment.

FIG. 3 shows a schematic block diagram illustrating a basic arrangement 300 of exemplary feedback paths according to the embodiment. Components 310, 325, 330 and 335, respectively, correspond to the components 210, 225, 230 and 235, respectively, as shown in FIG. 2. That is, the reference numeral 310 denotes an acquisition unit or receiver, the reference numerals 325 and 330 denote data and control buffer units serving as a "rubber band", and the reference numeral 335 denotes a backup control unit or method for controlling one or more acquisition units or receivers when the quality of service becomes so low that the control information from a central control unit is missing at some point. A reference numeral 345 denotes an actual (wireless) lossy communication or transport medium, i.e. the communication link. A reference numeral 350 denotes an experiment control, i.e. a data acquisition system that may control an experiment such as a MR experiment and can slow it down when required to reduce future bandwidth demands of the lossy communication medium data transport. This experiment control corresponds to the control device 140 in FIG. 1.

A reference numeral 355 denotes a local feedback loop, and a reference numeral 360 denotes a global feedback loop. As can be gathered from FIG. 3, the local feedback loop 355 may extend from the data buffer unit 325 to the data acquisition unit 310. In the local feedback loop 355 a compression method and/or compression ratio can be determined based on a fill level and rate supplied by the data buffer unit 325, and fed back to the data acquisition unit 310. As apparent from FIG. 3, the global feedback loop 360 may extend from the data buffer unit 325 to the experiment control 350. It partially overlaps the local feedback loop 355 in FIG. 3, as both of these feedback loops can be used simultaneously. In the global feedback loop 360 measures for at least momentarily reducing a data acquisition rate can be determined based on a fill level and rate supplied by the data buffer unit 325, and fed back to the experiment control 350 in order to reduce a future bandwidth demand.

Figure 4:
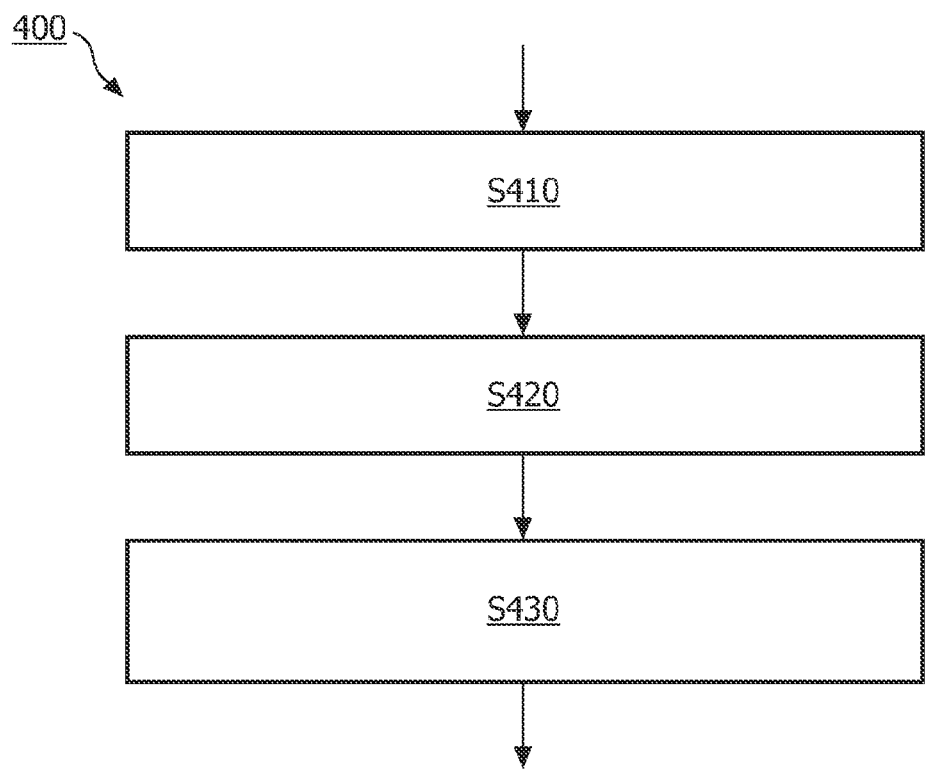
FIG. 4 shows a flowchart illustrating basic steps of an exemplary method according to the embodiment.

FIG. 4 shows a flowchart 400 illustrating basic steps of an exemplary method according to the embodiment. The method comprises a step S410 of acquiring examination data, a step S420 of transmitting the examination data via a communication link, and a step S430 of adapting a data rate of the examination data, based on an available quality of service of the communication link.

Figure 5:
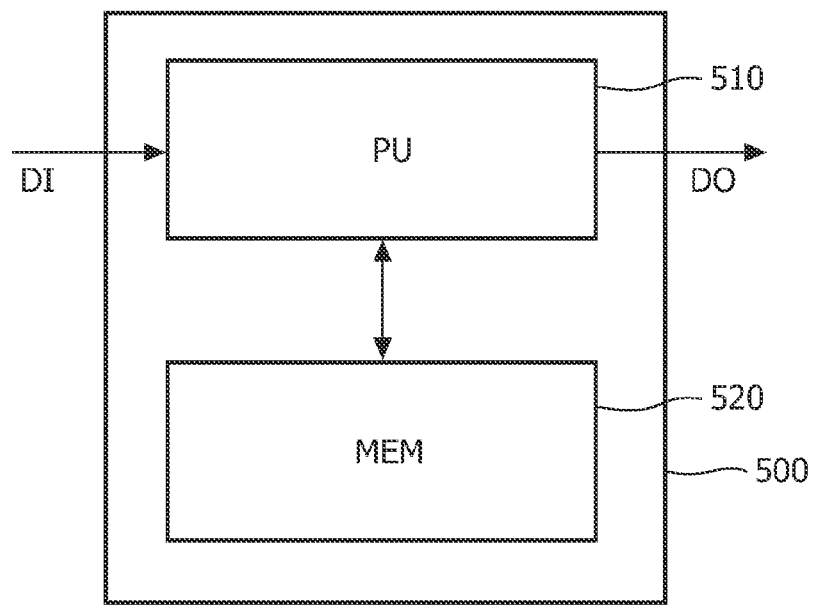
FIG. 5 shows an example of a software-based implementation of the embodiment.

FIG. 5 shows an example of a software-based implementation of the embodiment. Here, a device 500 comprises a processing unit (PU) 510, which may be provided on a single chip or a chip module and which may be any processor or computer device with a control unit that performs control based on software routines of a control program stored in a memory (MEM) 520. Program code instructions are fetched from the MEM 520 and loaded into the control unit of the PU 510 in order to perform processing steps such as those described in connection with FIG. 4. The processing steps of the blocks S410 to S430 may be performed on the basis of input data DI and may generate output data DO, wherein the input data DI may correspond to e.g. a signal such as a MR signal, and the output data DO can correspond to e.g. settings of an acquisition unit.

In summary, the present invention relates to a data rate controlling feedback loop that can evaluate an actual instantaneous available quality of service of a communication link for transmitting data and control the data rate based on an evaluation result. Feedback control may both be local to a device for acquiring examination data such as e.g. a magnetic resonance imaging coil or over the communication link by reducing the data rate at least momentarily to fit the communication link's performance over time, enabling a graceful degradation of an image quality at lower data rates.

While the present invention has been illustrated and described in detail in the drawings and foregoing description, such illustration and description are to be considered illustrative or exemplary and not restrictive. The invention is not limited to the disclosed embodiment. For example, the discussed adaptive data rate solution has been described with particular reference to MRI systems using wireless MRI coils. However, it is to be appreciated that the invention can also be applied in conjunction with other kinds of systems utilizing wireless communications, for example alternative types of examination or imaging systems such as e.g. x-ray systems. It may even find application in other arts and for wired communications.

Variations to the disclosed embodiment can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

A computer program capable of controlling a processor to perform the claimed features can be stored/distributed on a suitable medium, such as an optical storage medium or a solid-state medium supplied together with or as part of other hardware, but may also be distributed in other forms, such as via the Internet or other wired or wireless telecommunication systems. It can be used in conjunction with a new system such as e.g. a MRI system or other imaging system, but may also be applied when updating or upgrading existing systems in order to enable them to perform the claimed features.

A computer program product for a computer can comprise software code portions for performing e.g. processing steps such as those described in connection with FIG. 4 when the computer program product is run on the computer. The computer program product may further comprise a computer-readable medium on which the software code portions are stored, such as e.g. an optical storage medium or a solid-state medium.

Any reference signs in the claims should not be construed as limiting the scope thereof.

The invention claimed is:

1. A device comprising;
   an acquisition unit configured to acquire examination data;
   a communication unit configured to transmit said examination data via a communication link and receive control information via said communication link; and
   an adaptation unit configured to adapt a data rate of said examination data, based on an available quality of service of said communication link,
   wherein said acquisition unit and/or said adaptation unit is configured to be controlled based on said control information, and
   wherein said adaptation unit is configured to instruct said acquisition unit to perform no compression or a lossless compression of said examination data if said available quality of service is a certain limit and instruct said acquisition unit to perform a lossless compression with a higher compression ratio than in case of said available quality of service being above said certain limit or a lossy compression of said examination data if said available quality of service is equal to or below said certain limit.

2. The device according to claim 1, wherein said acquisition unit is configured to perform a compression of said examination data, and said adaptation unit is configured to adapt a degree of said compression.

3. The device according to claim 1, wherein said adaptation unit is configured to adapt an acquisition rate of said acquisition unit.

4. The device according to claim 1, wherein said adaptation unit is configured to instruct said acquisition unit to drop at least one examination data acquisition window.

5. The device according to claim 1, wherein said device is a wireless magnetic resonance imaging coil.

6. A system comprising:
   at least one device according to claim 1; and
   a control device configured to transmit control information to said at least one device and receive said examination data from said at least one device.

7. The system according to claim 6, wherein said control device is configured to throttle said communication link if said available quality of service is equal to or below a first threshold, and said adaptation unit is configured to perform a local reduction of said data rate if said available quality of service is equal to or below a second threshold.

8. The system according to claim 6, wherein said system is a magnetic resonance imaging system, and said control device is configured to control an acquisition rate of said at least one device by at least one of changing future acquisition transmission cycles of said examination data and changing a current supplied to magnetic field gradient coils of said magnetic resonance imaging system.

9. A device comprising:
   an acquisition unit configured to acquire examination data;
   a communication unit configured to transmit said examination data via a communication link and receive control information via said communication link; and
   an adaptation unit configured to adapt a data rate of said examination data, based on an available quality of service of said communication link,
   wherein said acquisition unit and/or said adaptation unit is configured to be controlled based on said control information, and
   wherein said adaptation unit is configured to adapt a compression ratio of said examination data if said available quality of service is equal to or below a first limit and adapt an acquisition rate of said acquisition unit if said available quality of service is equal to or below a second limit.

10. A device comprising:
    an acquisition unit configured to acquire examination data;
    a communication unit configured to transmit said examination data via a communication link and receive control information via said communication link;
    an adaptation unit configured to adapt a data rate of said examination data, based on an available quality of service of said communication link, wherein said acquisition unit and/or said adaptation unit is configured to be controlled based on said control information; and
a data buffer unit configured to buffer said examination data and supply as fill rate and level,
wherein said communication unit is configured to transmit said buffered examination data, and
wherein said adaptation unit is configured to determine said available quality of service based on said fill rate and level supplied by said data buffer unit.

11. A device comprising:
an acquisition unit configured to acquire examination data;
a communication unit configured to transmit said examination data via a communication link and receive control information via said communication link;
an adaptation unit configured to adapt a date rate of said examination data, based on an available quality of service of said communication link, wherein said acquisition unit and/or said adaptation unit is configured to be controlled based on said control information;
a control buffer unit configured to buffer said received control information and supply a fill rate and level; and
a backup control unit configured to determine said available quality of service based on said fill rate and level supplied by said control buffer unit, a certain whether said available quality of service is below a backup limit and control said acquisition unit if said ascertainment is affirmative,
wherein said acquisition unit is configured to be controlled based on said buffered control information.

12. A method comprising the acts of:
acquiring examination data by an acquisition unit;
transmitting said examination data via a communication link; and
adapting a data rate of said examination data by an adaptation unit, based on an available quality of service of said communication link,
wherein said adaptation unit is configured to one of:
instruct said acquisition unit to perform no compression or a lossless compression of said examination data if said available quality of service is above a certain limit and instruct said acquisition unit to perform a lossless compression with a higher compression ratio than in case of said available quality of service being above said certain limit or a lossy compression of said examination data if said available quality of service is equal to or below said certain limit,
adapt a compression ratio of said examination data if said available quality of service is equal to or below a first limit and adapt an acquisition rate of said acquisition unit if said available quality of service is equal to or below a second limit, and
determine said available quality of service based on a fill rate and level supplied by a data buffer unit configured to buffer said examination data.

13. A non-transitory computer readable medium embodying computer instructions which, when executed by a processor, configure the processor to perform the method of claim 12.

14. A method comprising the acts of:
acquiring examination data by an acquisition unit;
transmitting said examination data via a communication link;
receive control information via said communication link;
adapting a data rate of said examination data by an adaptation unit, based on an available quality of service of said communication link;
buffering said received control information by a control buffer unit;
supplying a fill rate and level by the control buffer unit;
determining said available quality of service based on said fill rate an the level supplied by said control buffer unit;
ascertaining whether said available quality of service is below a backup limit and controlling said acquisition unit if said ascertainment is affirmative,
wherein said acquisition unit is configured to be controlled based on said buffered control information.

* * * * *